(12) United States Patent
Kuramoto et al.

(10) Patent No.: US 11,377,512 B2
(45) Date of Patent: Jul. 5, 2022

(54) HYDROPHILIC COPOLYMER AND MEDICAL DEVICE

(71) Applicant: TERUMO KABUSHIKI KAISHA, Tokyo (JP)

(72) Inventors: Masanori Kuramoto, Kanagawa (JP); Takao Anzai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 174 days.

(21) Appl. No.: 16/282,929

(22) Filed: Feb. 22, 2019

(65) Prior Publication Data

US 2019/0185776 A1 Jun. 20, 2019

Related U.S. Application Data

(63) Continuation of application No. PCT/JP2017/029825, filed on Aug. 21, 2017.

(30) Foreign Application Priority Data

Aug. 25, 2016 (JP) .............................. JP2016-164815

(51) Int. Cl.
| | |
|---|---|
| *C08F 220/58* | (2006.01) |
| *A61L 31/10* | (2006.01) |
| *A61L 29/08* | (2006.01) |
| *C08F 220/38* | (2006.01) |
| *C10M 107/46* | (2006.01) |
| *C10M 107/48* | (2006.01) |
| *C10N 40/00* | (2006.01) |

(52) U.S. Cl.
CPC ............ *C08F 220/58* (2013.01); *A61L 29/08* (2013.01); *A61L 29/085* (2013.01); *A61L 31/10* (2013.01); *C08F 220/387* (2020.02); *C08F 220/585* (2020.02); *C10M 107/46* (2013.01); *C10M 107/48* (2013.01); *A61L 2400/10* (2013.01); *C08F 220/382* (2020.02); *C08F 2800/10* (2013.01); *C10M 2221/025* (2013.01); *C10M 2225/025* (2013.01); *C10N 2040/50* (2020.05)

(58) Field of Classification Search
CPC .............. C10M 107/48; C10M 107/43; C10M 2221/025; C10M 2225/025; A61L 29/08; A61L 29/085; A61L 31/10; A61L 2400/10; A61L 31/14; A61L 29/14; C08F 220/60; C08F 220/39; C08F 220/58; C08F 220/38; C08F 220/382; C08F 220/387; C08F 2800/10; C10N 2040/50; C09D 133/14

See application file for complete search history.

(56) References Cited

U.S. PATENT DOCUMENTS

| | | | |
|---|---|---|---|
| 5,702,754 A | 12/1997 | Zhong | |
| 6,780,930 B2 * | 8/2004 | Lewis | ............... C08F 246/00 524/800 |
| 7,645,504 B1 | 1/2010 | Pacetti | |
| 2008/0139746 A1 * | 6/2008 | Pacetti | ................... A61P 35/00 525/188 |
| 2011/0313077 A1 * | 12/2011 | Baba | ................... C08K 5/0008 523/107 |
| 2012/0059111 A1 | 3/2012 | Sandhu et al. | |
| 2014/0193474 A1 * | 7/2014 | Babcock | ............. A61L 29/085 428/476.3 |
| 2014/0350205 A1 | 11/2014 | Lerch et al. | |
| 2016/0015869 A1 | 1/2016 | Omata et al. | |
| 2016/0058919 A1 | 3/2016 | Minagawa et al. | |
| 2017/0182224 A1 * | 6/2017 | Babcock | ............. B05D 3/007 |

FOREIGN PATENT DOCUMENTS

| | | |
|---|---|---|
| CN | 105073155 A | 11/2015 |
| JP | S63258970 A | 10/1988 |
| JP | H05237377 A | 9/1993 |
| JP | H08109221 A | 4/1996 |
| JP | 2001139640 A | 5/2001 |
| JP | 2015-222445 A | 12/2015 |
| WO | 2009/099126 A1 | 8/2009 |
| WO | 2012150262 A1 | 11/2012 |

OTHER PUBLICATIONS

Office Action (Examination report No. 1 for standard patent application) dated Jun. 26, 2019, by the Australian Patent Office in corresponding Australian Patent Application No. 2017317423. (2 pages).

The extended European Search Report dated Mar. 17, 2020, by the European Patent Office in corresponding European Patent Application No. 17843543.4-1107. (9 pages).

(Continued)

*Primary Examiner* — Jessica M Roswell

(74) *Attorney, Agent, or Firm* — Buchanan Ingersoll & Rooney PC

(57) ABSTRACT

A hydrophilic copolymer that can form a surface lubricious layer exhibiting superior lubricating property and durability (lubrication retaining property), is provided. A hydrophilic copolymer having a good solvent solubility is provided. A hydrophilic copolymer is provided containing: structural units derived from a polymerizable monomer (A) having a sulfobetaine structure; structural units derived from a polymerizable monomer (B) having at least one group selected from the group consisting of a sulfonic acid group ($—SO_3H$), a sulfuric acid group ($—OSO_3H$), a sulfurous acid group ($—OSO_2H$), and groups of salts thereof; and structural units derived from a polymerizable monomer (C) having a photoreactive group.

12 Claims, 3 Drawing Sheets

(56) References Cited

OTHER PUBLICATIONS

International Search Report (PCT/ISA/210) dated Nov. 7, 2017, by the Japanese Patent Office as the International Searching Authority for International Application No. PCT/JP2017/029825.
Written Opinion (PCT/ISA/237) dated Nov. 7, 2017, by the Japanese Patent Office as the International Searching Authority for International Application No. PCT/JP2017/029825.
Lin, Xiaojie, et al., "Photoreactive Polymers Bearing a Zwitterionic Phosphorylcholine Group for Surface Modification of Biomaterials", ACS Applied Materials & Interfaces, 2015, No. 7, pp. 17489-17498.
An English Translation of the International Search Report (Form PCT/ISA/210) and the Written Opinion of the International Searching Authority (Form PCT/ISA/237) dated Nov. 7, 2017, by the Japanese Patent Office in corresponding International Application No. PCT/JP2017/029825. (6 pages).
Office Action dated Jan. 3, 2020, by the Intellectual Property Office of Singapore in corresponding Singapore Patent Application No. 11201901473U. (8 pages).
Office Action (First Examination Report) dated Feb. 1, 2021, by the Patent Office, Government of India, in corresponding India Patent Application No. 201917002986 with an English Translation of the Office Action. (5 pages).
Office Action (Notice of Reasons for Refusal) dated Jun. 15, 2021, by the Japanese Patent Office in corresponding Japanese Patent Application No. 2018-535669 and an English Translation of the Office Action. (8 pages).
Office Action (Notification of the First Office Action) dated Dec. 11, 2020, by the National Intellectual Property Administration, PRC in corresponding Chinese Patent Application No. 201780050953.0 and an English Translation of the Office Action. (12 pages).

\* cited by examiner

[FIG.1]
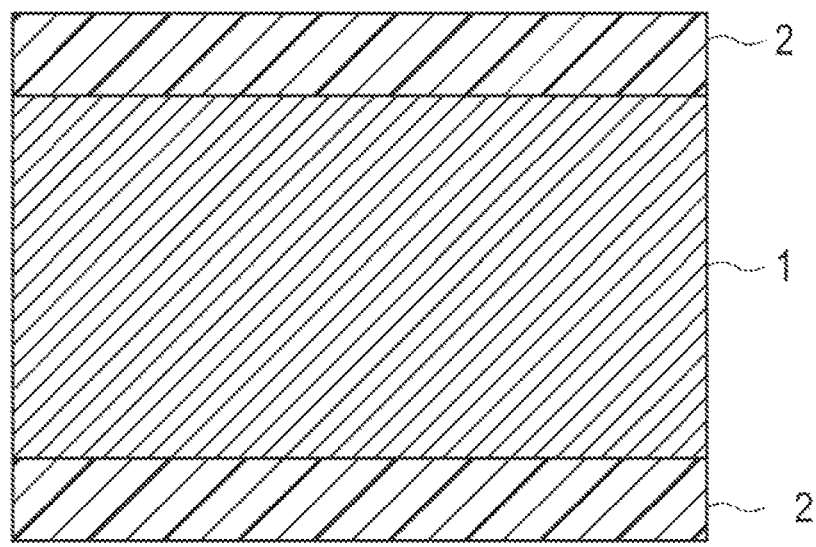
[FIG.2]
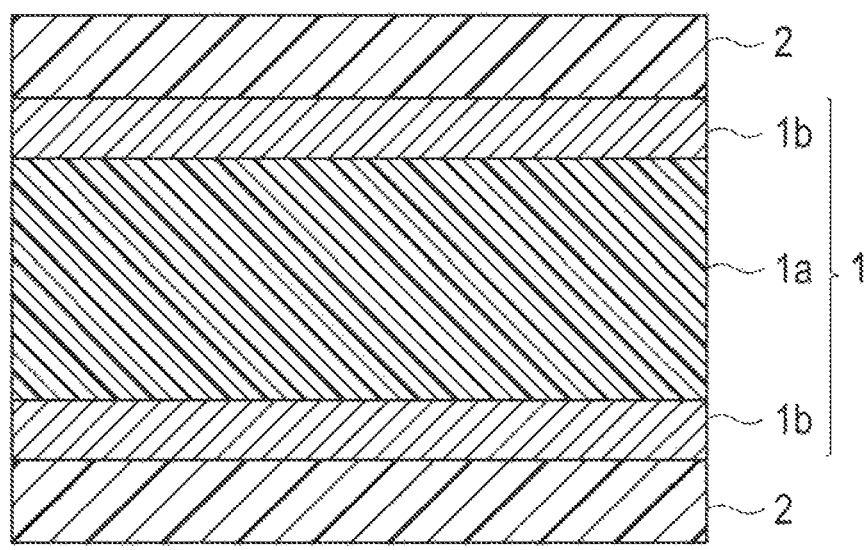

[FIG.3]
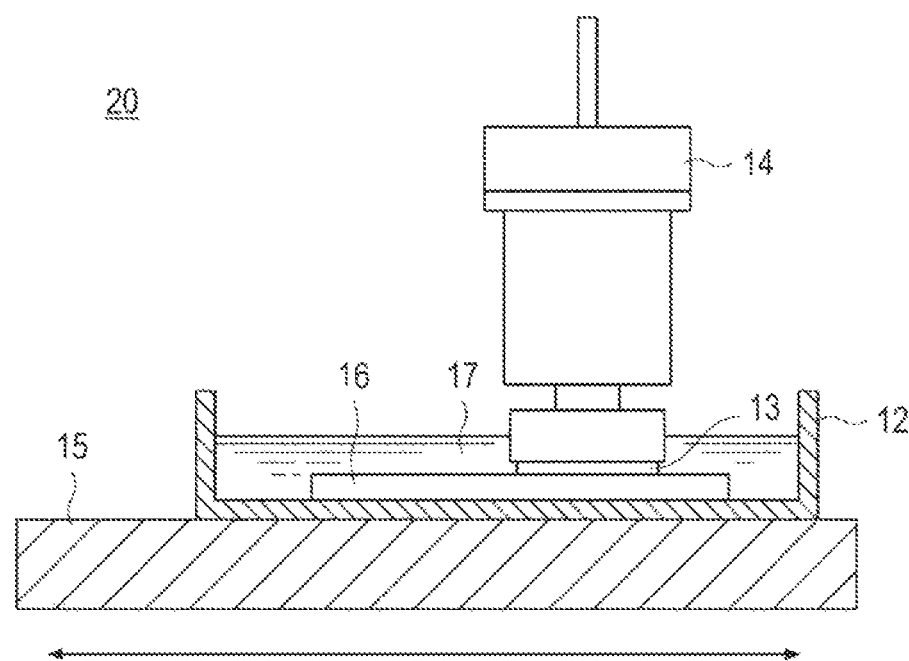
[FIG.4]
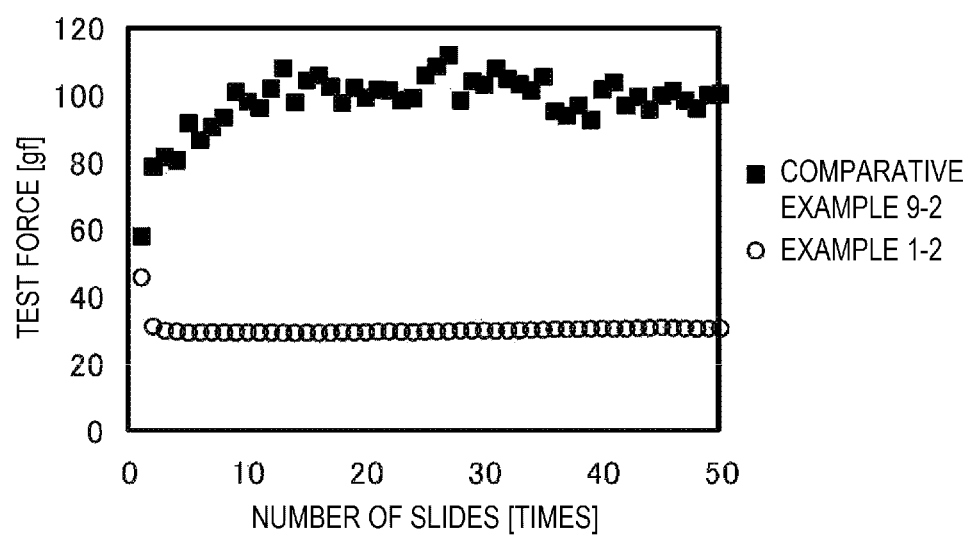

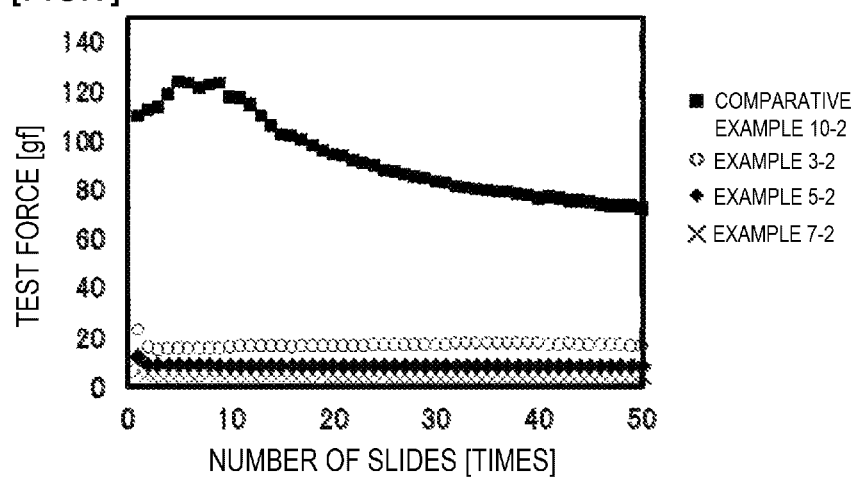

HYDROPHILIC COPOLYMER AND MEDICAL DEVICE

CROSS-REFERENCES TO RELATED APPLICATIONS

This application is a continuation of International Application No. PCT/JP2017/029825 filed on Aug. 21, 2017, which claims the benefit of priority of Japanese Application No. 2016-164815 filed on Aug. 25, 2016, the entire contents of which are incorporated herein by reference.

TECHNICAL FIELD

Disclosed are a hydrophilic copolymer and a medical device having a surface lubricious layer containing the hydrophilic copolymer.

BACKGROUND DISCUSSION

In recent years, diameters of catheters have been progressively reduced for accessing peripheral lesions. This leads to a significant decrease of the clearance between a catheter and the interior surface of a lumen in a living body to cause high frictional resistance on the surface of the catheter. Thus, there is a need for a coating for imparting lubricating property and durability (lubrication retaining property) to a surface of a catheter.

In addition, when a coating is applied on a substrate of a catheter or the like, a solvent having low toxicity, such as water, an alcohol, or a water/alcohol mixed solvent, can be selected as the solvent thereof in terms of compatibility with biological materials and safety of the operator. Thus, the components of the coating can dissolve or disperse in such solvents (to have solvent solubility).

ACS Appl. Mater. Interface, 2015, 7(31), pp. 17489-17498 discloses as a surface modifier for biological materials a copolymer of 2-methacryloyloxyethyl phosphorylcholine (MPC) which is a polymerizable monomer having a phosphobetaine structure and 4-methacryloyloxybenzophenone (MBP) which is a polymerizable monomer having a photoreactive group.

SUMMARY

However, a surface lubricious layer containing the copolymer described in ACS Appl. Mater. Interface, 2015, 7(31), pp. 17489-17498 cannot exhibit sufficient lubricating property and durability (lubrication retaining property).

Accordingly, an exemplary aspect of the present disclosure is to provide a hydrophilic copolymer that can form a surface lubricious layer exhibiting superior lubricating property and durability (lubrication retaining property). Another exemplary aspect of the present disclosure is to provide a hydrophilic copolymer having good solvent solubility.

The present inventors have made intensive and extensive studies for addressing or solving the above problems. As a result, for example, they have found that exemplary aspects can be achieved by a hydrophilic copolymer containing: structural units derived from a polymerizable monomer (A) having a sulfobetaine structure; structural units derived from a polymerizable monomer (B) having at least one group selected from the group consisting of a sulfonic acid group ($-SO_3H$), a sulfuric acid group ($-OSO_3H$), a sulfurous acid group ($-OSO_2H$), and groups of salts thereof; and structural units derived from a polymerizable monomer (C) having a photoreactive group.

BRIEF DESCRIPTION OF THE DRAWINGS

FIG. 1 is a partial cross sectional view schematically illustrating a surface lamination structure of an exemplary embodiment of a medical device. In FIG. 1, 1 denotes a substrate layer, 2 denotes a surface lubricious layer, and 10 denotes a medical device.

FIG. 2 is a partial cross sectional view schematically illustrating a different configuration example of a surface lamination structure. In FIG. 2, 1 denotes a substrate layer, 1a denotes a substrate layer core, 1b denotes a substrate surface layer, 2 denotes a surface lubricious layer, and 10 denotes a medical device.

FIG. 3 is a schematic diagram of an exemplary lubricating property and durability testing device (friction meter) used in Example 1-2 and Comparative Example 9-2. In FIG. 3, 12 denotes a petri dish, 13 denotes an HDPE terminal, 14 denotes a load, 15 denotes a moving table, 16 denotes an HDPE sheet (sample), 17 denotes water, and 20 denotes a friction meter.

FIG. 4 is a figure showing results of the lubricating property and durability test in Example 1-2 and Comparative Example 9-2.

FIG. 5 is a figure showing results of the lubricating property and durability test in Example 3-2, Example 5-2, Example 7-2, and Comparative Example 10-2.

DETAILED DESCRIPTION

An exemplary embodiment will be described in detail below. Note that the present disclosure is not limited only to the embodiment. As used herein, "X to Y" which represents a range includes X and Y, that is, the phrase means "X or more and Y or less". Unless otherwise specified, operations and measurements of physical properties and the like are made under conditions at room temperature (20 to 25° C.) and a relative humidity of 40 to 60%.

As used herein, the term "(meth)acryl" includes both of acryl and methacryl. Thus, for example, the term "(meth)acrylic acid" includes both of acrylic acid and methacrylic acid. Similarly, the "(meth)acryloyl" includes both of acryloyl and methacryloyl. Thus, for example, the term "(meth)acryloyl group" includes both of acryloyl group and methacryloyl group.

Unless otherwise defined, the term "substituted", as used herein refers to being substituted by a C1-C30 alkyl group, a C2-C30 alkenyl group, a C2-C30 alkynyl group, a C1-C30 alkoxy group, an alkoxycarbonyl group (—COOR, R is a C1-C30 alkyl group), a halogen atom (F, Cl, Br, or I atom), a C6-C30 aryl group, a C6-C30 aryloxy group, an amino group, a C1-C30 alkylamino group, a cyano group, a nitro group, a thiol group, a C1-C30 alkylthio group, or a hydroxyl group. Note that the term "substituted" does not include a substituent from the above list in which the substituent is further substituted with another substituent from the above list. For example, when an alkyl group is a substituent, the alkyl group as the substituent is not further substituted by another alkyl group.

As used herein, the phrase "a structural unit is derived from a monomer" means that in the case the structural unit is a divalent structural unit, the divalent structural unit is produced by cutting one bond of a polymerizable unsaturated double bond in a corresponding monomer.

<Hydrophilic Copolymer>

The hydrophilic copolymer contains: structural units derived from a polymerizable monomer (A) having a sulfobetaine structure (hereinafter also referred to as "monomer A"); structural units derived from a polymerizable monomer (B) having at least one group selected from the group consisting of a sulfonic acid group (—$SO_3H$), a sulfuric acid group (—$OSO_3H$), a sulfurous acid group (—$OSO_2H$), and groups of salts thereof (hereinafter also referred to as "monomer B"); and structural units derived from a polymerizable monomer (C) having a photoreactive group (hereinafter also referred to as "monomer C"). The hydrophilic copolymer can form a surface lubricious layer exhibiting superior lubricating property and durability (lubrication retaining property). In addition, the hydrophilic copolymer has good solvent solubility. The mechanism of causing the exemplary effects has not been completely understood, but is supposed as follows.

Without being bound by any particular theory, for example, the photoreactive group contained in a structural unit derived from the monomer C may produce a reactive species by irradiation with an active energy ray, and may react with a substrate layer surface to form a chemical bond. Thus, a surface lubricious layer containing the hydrophilic copolymer according to an exemplary aspect is strongly fixed on a substrate layer, thereby exhibiting superior durability (lubrication retaining property).

In addition, the sulfobetaine structure contained in a structural unit derived from the monomer A is superior in lubricating property imparting effect as compared with other betaine structures, such as a phosphobetaine structure. Thus, a surface lubricious layer containing the hydrophilic copolymer according to an exemplary aspect (Example 1-2) can exhibit superior lubricating property as compared with a surface lubricious layer containing the copolymer described in ACS Appl. Mater. Interface, 2015, 7(31), pp. 17489-17498 (Comparative Example 9-2) (FIG. 4). Homopolymers from monomers having a phosphobetaine structure are soluble in water, whereas a study of the present inventors has revealed that homopolymers from the monomer A are soluble in aqueous NaCl solutions but do not or hardly dissolve in water and lower alcohols. The difference in the water solubility suggests a possibility of higher electrostatic interaction of sulfobetaine structures than that of phosphobetaine structures. Thus, a strong cohesive force is caused inside a surface lubricious layer containing the hydrophilic copolymer according to an exemplary aspect. This results in enhancement of the strength of the surface lubricious layer so that the surface lubricious layer is hardly peeled and can maintain initial lubricating property even after repetitive slides. Accordingly, a surface lubricious layer containing the hydrophilic copolymer according to an exemplary aspect (Example 1-2) can also exhibit superior durability (lubrication retaining property) as compared with a surface lubricious layer containing the copolymer described in ACS Appl. Mater. Interface, 2015, 7(31), pp. 17489-17498 (Comparative Example 9-2) (FIG. 4).

However, the present inventors encountered the problem in that copolymers of the monomer A and the monomer C (in particular, a monomer having a benzophenone group) do not or hardly dissolve or disperse in various solvents, such as water, aqueous NaCl solutions, lower alcohols, and water/lower alcohols (that is, has extremely low solvent solubility) and therefore are difficult to apply to coatings. Regarding this problem, with an assumption that the problem may be caused by both the electrostatic interaction between the sulfobetaine structures and the hydrophobic interaction between the photoreactive groups simultaneously occurring between polymer molecules, the present inventors focused on the monomer B as a third copolymerization component in an exemplary aspect. A sulfonic acid group, a sulfuric acid group, a sulfurous acid group, or a group of a salt thereof contained in the structural unit derived from the monomer B is easily anionized in aqueous solvents. This causes electrostatic repulsion between polymer molecules to reduce the aforementioned interactions so that the polymer becomes likely to dissolve or disperse in aqueous solvents. Thus, the hydrophilic copolymer according to an exemplary aspect has superior solvent solubility. The effect of enhancing solvent solubility given by the monomer B is especially notable when the photoreactive group in the monomer C is a benzophenone group. A benzophenone group has plural aromatic rings and therefore is likely to associate due to the n-n interaction. Thus, a polymer containing a benzophenone group easily aggregates to become insoluble. Thus, when structural units derived from the monomer B are incorporated, electrostatic repulsion occurs as described above to suppress the association of benzophenone groups, thereby dramatically increasing solubility or dispersibility of the polymer.

Note that the above mechanism is merely an assumption, and the present disclosure is not limited to the assumption.

Polymerizable monomers constituting the hydrophilic copolymer according to an exemplary aspect will be described below.

[Polymerizable Monomers]

(Monomer A)

The monomer A is a polymerizable monomer having a sulfobetaine structure. The "sulfobetaine structure" as used herein refers to a structure where a positive charge and a negative charge containing a sulfur element are present at positions that are not adjacent to each other, an atom having a positive charge has no hydrogen atom that can be released, and the total sum of the charges is zero.

Examples of the monomers A include, but are not limited to, compounds represented by the following general formulae:

[Chem. 1]

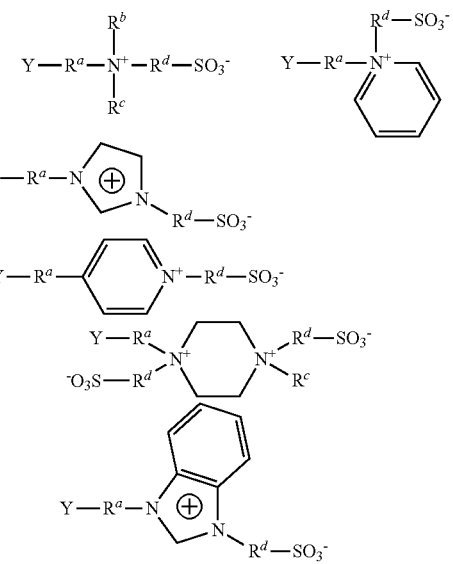

In the above general formulae, $R^a$ and $R^d$ may each independently be an alkylene group having 1 to 30 carbon atoms which may be substituted or an arylene group having 6 to 30 carbon atoms which may be substituted, $R^b$ and $R^e$ may each independently be an alkyl group having 1 to 30 carbon atoms which may be substituted or an aryl group having 6 to 30 carbon atoms which may be substituted, and Y may be an ethylenically unsaturated group, such as an acryloyl group, a methacryloyl group, or a vinyl group. In the general formulae, the total sum of positive charges and negative charges is zero.

Examples of alkylene groups having 1 to 30 carbon atoms include a methylene group, an ethylene group, a triethylene group, a propylene group, an isopropylene group, a butylene group, an isobutylene group, a sec-butylene group, a tert-butylene group, and a pentylene group.

Examples of arylene groups having 6 to 30 carbon atoms include a phenylene group, a naphthylene group, an anthracenylene group, a phenanthrenylene group, a pyrenylene group, a perylenylene group, a fluorenylene group, and a biphenylene group.

Examples of alkyl groups having 1 to 30 carbon atoms include a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, a neopentyl group, and an n-hexyl group.

Examples of aryl groups having 6 to 30 carbon atoms include a phenyl group, a biphenyl group, a terphenyl group, a pentalenyl group, an indenyl group, a naphthyl group, an azulenyl group, a heptalenyl group, and a biphenylenyl group.

Among them, the monomer A can be a compound represented by the following formula (1) from the viewpoint of further enhancement of lubricating property and durability (lubrication retaining property):

[Chem. 2]

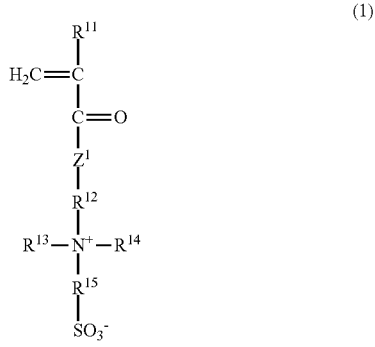

(1)

In the formula (1), $R^{11}$ is a hydrogen atom or a methyl group. $Z^1$ is an oxygen atom (—O—) or —NH—, for example, an oxygen atom (—O—).

In the formula (1), $R^{12}$ and $R^{15}$ are each independently a straight chain or branched chain alkylene group having 1 to 20 carbon atoms from the viewpoint of further enhancement of lubricating property and durability (lubrication retaining property), for example, a straight chain or branched chain alkylene group having 1 to 12 carbon atoms, for example, a straight chain or branched chain alkylene group having 1 to 8 carbon atoms, for example, a straight chain or branched chain alkylene group having 1 to 6 carbon atoms, for example, a straight chain alkylene group having 1 to 3 carbon atoms (a methylene group, an ethylene group, or a trimethylene group).

In the formula (1), $R^{13}$ and $R^{14}$ are each independently a straight chain or branched chain alkyl group having 1 to 20 carbon atoms from the viewpoint of further enhancement of lubricating property and durability (lubrication retaining property), for example, a straight chain or branched chain alkyl group having 1 to 12 carbon atoms, for example, a straight chain or branched chain alkyl group having 1 to 8 carbon atoms, for example, a straight chain or branched chain alkyl group having 1 to 4 carbon atoms, for example, a methyl group.

Examples of compounds represented by the formula (1) include {2-[(meth)acryloyloxy]ethyl}dimethyl-(3-sulfopropyl)ammonium hydroxide, {2-[(meth)acryloyloxy]ethyl}dimethyl-(2-sulfoethyl)ammonium hydroxide, {2-[(meth)acryloyloxy]ethyl}diethyl-(2-sulfoethyl)ammonium hydroxide, {2-[(meth)acryloyloxy]ethyl}diethyl-(3-sulfopropyl)ammonium hydroxide, {3-[(meth)acryloyloxy]propyl}dimethyl-(2-sulfoethyl)ammonium hydroxide, {3-[(meth)acryloyloxy]propyl}dimethyl-(3-sulfopropyl)ammonium hydroxide, {3-[(meth)acryloyloxy]propyl}diethyl-(2-sulfoethyl)ammonium hydroxide, and {3-[(meth)acryloyloxy]propyl}diethyl-(3-sulfopropyl)ammonium hydroxide, and among them, {2-[(meth)acryloyloxy]ethyl}dimethyl-(3-sulfopropyl)ammonium hydroxide and [3-(methacryloylamino)propyl]dimethyl(3-sulfopropyl)ammonium hydroxide are exemplary. The above compounds may be used alone or in combination of two or more thereof.

The monomer A used may be either of a synthetic compound or a commercially available product. A commercially available product is available from Sigma-Aldrich Co. LLC., for example. An exemplary compound may be synthesized in view of A. Laschewsky, Polymers, 6, 1544-1601 (2014), for example.

The monomer A is not limited to the compound represented by the aforementioned general formulae, and may be a compound that has a form having a positive charge at an end thereof.

In the hydrophilic copolymer, the content of the structural units derived from the monomer A, based on 100% by mole of the total of the structural units derived from all monomers, can be 0.05 to 99% by mole, for example, 0.1 to 98% by mole, for example, 0.1 to 95% by mole, for example, 0.1 to 90% by mole. In such a range, a good balance between the lubricating property and the solvent solubility can be achieved. The molar percentage can be substantially equal to the proportion of the amount (moles) of the monomer A supplied based on the total amount (moles) of all the monomers supplied in production of the polymer.

(Monomer B)

The monomer B is a polymerizable monomer having at least one group selected from the group consisting of a sulfonic acid group (—$SO_3H$), a sulfuric acid group (—$OSO_3H$), a sulfurous acid group (—$OSO_2H$), and groups of salts thereof. With such a group incorporated, electrostatic repulsion can occur between hydrophilic copolymer molecules. Thus, the solvent solubility of the copolymer can be enhanced. This effect of enhancement can be particularly notable when the photoreactive group in the monomer C is a benzophenone group. Alternatively, also when the monomer C contains an ester group, the above effect of enhancement can be obtained well. The monomer B can have, in addition to the aforementioned groups, an ethylenically unsaturated group, such as a (meth)acryloyl group, a vinyl group, or an aryl group.

Among them, from the viewpoint of further enhancement of the solvent solubility, the monomer B can be a compound represented by the following formula (2), (3), or (4), for example, a compound represented by the following formula (2).

[Chem. 3]

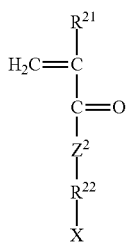

(2)

In the formula (2), $R^{21}$ is a hydrogen atom or a methyl group. $Z^2$ is an oxygen atom (—O—) or —NH—, for example, —NH—.

In the formula (2), $R^{22}$ is a straight chain or branched chain alkylene group having 1 to 20 carbon atoms from the viewpoint of further enhancement of the solvent solubility, for example, a straight chain or branched chain alkylene group having 1 to 12 carbon atoms, for example, a straight chain or branched chain alkylene group having 1 to 8 carbon atoms, for example, a straight chain or branched chain alkylene group having 1 to 6 carbon atoms, for example, a branched chain alkylene group having 3 to 5 carbon atoms. The branched chain alkylene group having 3 to 5 carbon atoms is a group represented by, for example, —CH(CH$_3$)—CH$_2$—, —C(CH$_3$)$_2$—CH$_2$—, —CH(CH$_3$)—CH(CH$_3$)—, —C(CH$_3$)$_2$—CH$_2$—CH$_2$—, —CH(CH$_3$)—CH(CH$_3$)—CH$_2$—, —CH(CH$_3$)—CH$_2$—CH(CH$_3$)—, —CH$_2$—C(CH$_3$)$_2$—CH$_2$—, or —C(CH$_3$)$_2$—CH(CH$_3$)— (provided that, the order of linking of the above group in the formula (2) is not limited), and among them, a group represented by —C(CH$_3$)$_2$—CH$_2$— is exemplary.

In the formula (2), X is a group selected from the group consisting of a sulfonic acid group (—SO$_3$H), a sulfuric acid group (—OSO$_3$H), a sulfurous acid group (—OSO$_2$H), and groups of salts thereof, and from the viewpoint of the degree of acid dissociation (that is, the degree of easiness of anionization) and in turn the solvent solubility of the copolymer, X can be a group selected from the group consisting of a sulfonic acid group, a sulfuric acid group, and groups of salts thereof, and in terms of the availability of the monomer, X can be a sulfonic acid group or a group of a salt thereof.

Examples of compounds represented by the formula (2) include 2-(meth)acrylamide-2-methyl-1-propanesulfonic acid, 1-[(meth)acryloyloxymethyl]-1-propanesulfonic acid, 2-[(meth)acryloyloxy]-2-propanesulfonic acid, 3-[(meth)acryloyloxy]-1-methyl-1-propanesulfonic acid, 2-sulfoethyl (meth)acrylate, 3-sulfopropyl (meth)acrylate, and salts thereof. The compounds may be used alone or in combination of two or more thereof.

The compound represented by the formula (2) used may be either of a synthetic compound or a commercially available product, and a commercially available product may be available, for example, from Tokyo Chemical Industry, Co., Ltd.

[Chem. 4]

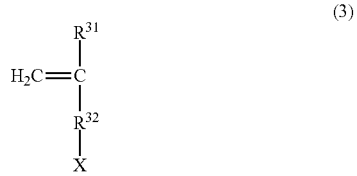

In the formula (3), $R^{31}$ is a hydrogen atom or a methyl group.

In the formula (3), $R^{32}$ is a single bond or a straight chain or branched chain alkylene group having 1 to 20 carbon atoms, for example, a single bond or a straight chain or branched chain alkylene group having 1 to 12 carbon atoms, for example, a single bond or a straight chain or branched chain alkylene group having 1 to 8 carbon atoms, for example, a single bond or a straight chain or branched chain alkylene group having 1 to 4 carbon atoms, for example, a single bond. Examples of alkylene groups here are the same as in the formula (2) and therefore the description is omitted here.

In the formula (3), X is a group selected from the group consisting of a sulfonic acid group (—SO$_3$H), a sulfuric acid group (—OSO$_3$H), a sulfurous acid group (—OSO$_2$H), and groups of salts thereof, and from the viewpoint of the degree of acid dissociation (that is, the degree of easiness of anionization) and in turn the solvent solubility of the copolymer, X can be a group selected from the group consisting of a sulfonic acid group and a sulfuric acid group, and groups of salts thereof, and in terms of the availability of the monomer, X can be a sulfonic acid group or groups of salts thereof.

Examples of compounds represented by the formula (3) include vinylsulfonic acid, allylsulfonic acid, methallylsulfonic acid, 2-propene-1-sulfonic acid, 2-methyl-2-propene-1-sulfonic acid, and salts thereof. The compounds may be used alone or in combination of two or more thereof.

The compound represented by the formula (3) used may be either of a synthetic compound or a commercially available product, and a commercially available product may be available from, for example, Asahi Kasei Finechem Co., Ltd., or Tokyo Chemical Industry, Co., Ltd. As a commercially available product, 2-methyl-2-propene-1-sulfonic acid sodium salt from Tokyo Chemical Industry, Co., Ltd. may be used.

[Chem. 5]

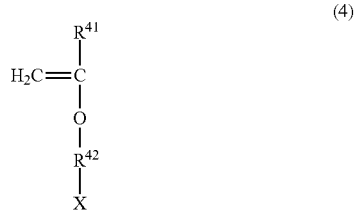

In the formula (4), $R^{41}$ is a hydrogen atom or a methyl group.

In the formula (4), $R^{42}$ is a straight chain or branched chain alkylene group having 1 to 20 carbon atoms, for example, a straight chain or branched chain alkylene group having 1 to 12 carbon atoms, for example, a straight chain or branched chain alkylene group having 1 to 8 carbon atoms, for example, a straight chain or branched chain alkylene group having 1 to 6 carbon atoms. Examples of alkylene groups here are the same as in the formula (2), and therefore the description is omitted here.

In the formula (4), X is a group selected from the group consisting of a sulfonic acid group (—$SO_3H$), a sulfuric acid group (—$OSO_3H$), a sulfurous acid group (—$OSO_2H$), and groups of salts thereof, and from the viewpoint of the degree of acid dissociation (that is, the degree of easiness of anionization) and in turn the solvent solubility of the copolymer, X can be a group selected from the group consisting of a sulfonic acid group, a sulfuric acid group, and groups of salts thereof, and in terms of the availability of the monomer, X can be a sulfonic acid group or a group of a salt thereof.

Examples of compounds represented by the formula (4) include 2-solfoxyethyl vinyl ether, 3-solfoxy-n-propyl vinyl ether, and salts thereof. The compounds may be used alone or in combination of two or more thereof.

The compound represented by the formula (4) used may be either of a synthetic compound or a commercially available product.

In the hydrophilic copolymer according to an exemplary aspect, the content of the structural units derived from the monomer B based on 100% by mole of the total of the structural units derived from all monomers can be 0.1 to 99% by mole, for example, 0.2 to 99% by mole, for example, 0.5 to 99% by mole, for example, 1 to 99% by mole, and for example, the content can be 20 to 99% by mole, for example, 25 to 99% by mole, for example, 28 to 99% by mole. In this range, a good balance of the lubricating property and the solvent solubility can be achieved. Note that the molar percentage can be substantially equal to the proportion of the amount (moles) of the monomer B supplied based on the total amount (moles) of all the monomers supplied in production of the polymer.

(Monomer C)

The monomer C is a polymerizable monomer having a photoreactive group. As used herein, the "photoreactive group" refers to a group that generates a reactive species, such as a radical, a nitrene, or a carbene when irradiated with an active energy ray, and can react with a substrate layer to form a chemical bond. Thus, a surface lubricious layer containing the hydrophilic copolymer according to an exemplary aspect can be strongly fixed on a substrate surface. Accordingly, the surface lubricious layer can exhibit superior durability (lubrication retaining property). In addition, the monomer C can have, in addition to the photoreactive group, an ethylenically unsaturated group, such as a (meth) acryloyl group, a vinyl group, or an allyl group.

Examples of photoreactive groups include an azide group, a diazo group, a diazirine group, a ketone group, and a quinone group.

Examples of azide groups include aryl azide groups, such as phenyl azide and 4-fluoro-3-nitrophenyl azide; acyl azide groups, such as benzoyl azide and p-methylbenzoyl azide; azideformate groups, such as ethyl azideformate and phenyl azideformate; sulfonyl azide groups, such as benzenesulfonyl azide; and phosphoryl azide groups, such as diphenylphosphoryl azide and diethylphosphoryl azide.

Examples of diazo groups include groups derived from, for example, diazoalkanes, such as diazomethane and diphenyldiazomethane; diazoketones, such as diazoacetophenone and 1-trifluoromethyl-1-diazo-2-pentanone; diazoacetates, such as t-butyl diazoacetate and phenyl diazoacetate; and β-keto-α-diazoacetoacetates, such as t-butyl-α-d iazoacetoacetate.

Examples of diazirine groups include groups derived from, for example, 3-trifluoromethyl-3-phenyldiazirine.

Examples of ketone groups include groups having a structure, such as acetophenone, benzophenone, anthrone, xanthine, or thioxanthone.

Examples of quinone groups include groups derived from, for example, anthraquinone.

The photoreactive group can be appropriately selected according to the type of the substrate layer of the medical device, and the like. For example, when the substrate layer is formed of a polyolefin resin, such as polyethylene resin, a polyamide resin, a polyurethane resin, a polyester resin, or the like, the photoreactive group can be a ketone group or a phenyl azide group, and in terms of the availability of the monomer, it can be a group having a benzophenone structure (a benzophenone group).

Examples of the monomers C include 2-azidoethyl (meth) acrylate, 2-azidopropyl (meth)acrylate, 3-azidopropyl (meth)acrylate, 4-azidobutyl (meth)acrylate, 4-(meth)acryloyloxybenzophenone, 4-(meth)acryloyloxyethoxybenzophenone, 4-(meth)acryloyloxy-4'-m ethoxybenzophenone, 4-(meth)acryloyloxyethoxy-4'-methoxybenzophenone, 4-(meth)acryloyloxy-4'-bromobenzophenone, 4-(meth) acryloyloxyethoxy-4'-bromobenzophenone, 4-styrylmethoxybenzophenone, and 4-(meth)acryloyloxythioxanthone.

The monomer C used may be either of a synthetic compound or a commercially available product, and a commercially available product may be available, for example, from MRC UNITEC Co., Ltd.

In the hydrophilic copolymer of an exemplary aspect, the content of the structural units derived from the monomer C based on 100% by mole of the total of the structural units derived from all monomers can be 0.1 to 40% by mole, for example, 0.1 to 30% by mole, for example, 0.1 to 25% by mole, for example, 0.1 to 20% by mole, for example, 0.5 to 15% by mole, for example, 0.8 to 12% by mole, for example, 1 to 10% by mole. For example, in the range, the hydrophilic copolymer can sufficiently bind to the substrate layer, and therefore the surface lubricious layer containing the hydrophilic copolymer can be strongly fixed to the substrate layer. For example, in the range, sufficient amounts of the other monomers (the monomers A and B) can exist, and therefore the hydrophilic copolymer can be effectively improved in the lubricating property and durability by the monomer A and the solvent solubility by the monomer B. The molar percentage can be substantially equal to the proportion of the amount (moles) of the monomer C supplied based on the total amount (moles) of all the monomers supplied in production of the polymer.

The hydrophilic copolymer according to an exemplary aspect may contain any structural units derived from other polymerizable monomers than the monomer A, the monomer B, and the monomer C (hereinafter also referred to as "other monomers"). For example, the other monomers can be present in an amount that does not impair the exemplary effects described above. In the hydrophilic copolymer according to an exemplary aspect, the content of the structural units derived from other monomers, based on 100% by mole of the total amount of structural units derived from all the monomer, can be less than 10% by mole, for example, less than 5% by mole, for example, less than 1% by mole (lower limit: 0% by mole). For example, the hydrophilic copolymer according to an exemplary embodiment can consist of the monomer A, the monomer B, and the monomer C. The molar percentage can be substantially equal to the proportion of the amount (moles) of the other monomers supplied based on the total amount (moles) of all the monomers supplied in production of the polymer.

The ends of the hydrophilic copolymer according to an exemplary aspect are not limited and can be appropriately defined according to the type of the material used. The ends can be hydrogen atoms. The structure of the copolymer is not limited and may be any of a random copolymer, an alternating copolymer, a periodical copolymer, and a block copolymer.

[Physical Properties of Hydrophilic Copolymer]

The hydrophilic copolymer according to an exemplary aspect can be superior in solvent solubility, and for example, is superior in solubility in water, lower alcohols, or mixed solvents of water and a lower alcohol. As used herein, the "lower alcohol" refers to an alcohol having 1 to 3 carbon atoms, that is, methanol, ethanol, n-propanol, or isopropanol. This can enable one to apply the solvents having low toxicity to a coating liquid, ensuring the safety of operators. In addition, solvents containing a lower alcohol can be quickly removed from the coated film because of their high vaporization speed. Thus, a drying step in coating of a medical device can be simplified and a coating operation can be performed quickly. Note that the "superior in solvent solubility" means that the copolymer dissolves or disperses in the above solvents, for example, in an amount of 1% by weight or more. The time required for dissolving or dispersion here can be within 2 hours.

The copolymer can have a weight average molecular weight of several thousands to several millions. The "weight average molecular weight" adopted in the present disclosure is a value measured by gel permeation chromatography (GPC) using polyethylene glycol as a standard.

[Method of Producing Hydrophilic Copolymer]

The method of producing the hydrophilic copolymer according to an exemplary aspect is not limited and polymerization methods, such as radical polymerization, anion polymerization, and cation polymerization may be used. Radical polymerization, which can allow for easy production, can be used.

An exemplary polymerization method that can be used is a method in which the monomer A, the monomer B, and the monomer C, and any other monomers used, are copolymerized by stirring and heating them together with a polymerization initiator in a polymerization solvent.

The polymerization temperature can be, but is not limited to, 25 to 100° C., for example, 30 to 80° C. The polymerization time can be, but is not limited to, 30 minutes to 24 hours, for example, 1 hour to 5 hours.

The polymerization solvent can be aqueous solvents, for example, water; alcohols, such as methanol, ethanol, propanol, n-butanol, and 2,2,2-trifluoroethanol; and polyhydric alcohols, such as ethylene glycol, diethylene glycol, propylene glycol, and dipropylene glycol. From the viewpoint of dissolving raw materials used in the polymerization, one of the solvents may be used alone or two or more thereof may be used in combination.

The concentrations of the polymerizable monomers can be, but are not limited to, 0.05 to 1 g/mL, for example, 0.1 to 0.5 g/mL in terms of the total solid amount (g) of the polymerizable monomers relative to the polymerization solvent (mL). Exemplary proportions of the amount (moles) of each monomer supplied based on the total amount (moles) of all the monomers supplied can be as described above.

The reaction solution containing the polymerizable monomers may be degassed before addition of a polymerization initiator. Degassing may be performed, for example, by bubbling an inert gas, such as nitrogen gas or argon gas, in the reaction solution for about 0.5 to 5 hours. In degassing, the reaction solution may be heated to about 30 to 100° C.

In production of the polymer, any suitable polymerization initiator may be used, and examples of polymerization initiators that can be used include, but are not limited to, azo-based polymerization initiators, such as 2,2'-azobisisobutyronitrile, 2,2'-azobis(4-methoxy-2,4-dimethylvaleronitrile), 4,4'-azobis(4-cyanovaleric acid), and 2,2'-azobis (2,4-dimethylvaleronitrile); and redox-type polymerization initiators in which an oxidant, for example, a persulfate, such as potassium persulfate (KPS), sodium persulfate, or ammonium persulfate, or a peroxide, such as hydrogen peroxide, t-butyl peroxide, or methyl ethyl ketone peroxide, is combined with a reductant, for example, sodium sulfite, sodium hydrogen sulfite, or ascorbic acid.

The amount of the polymerization initiator incorporated, based on the total amount (moles) of the polymerizable monomers, can be 0.01 to 10% by mole, for example, 0.1 to 5% by mole.

A chain transfer agent, a polymerization rate modifier, a surfactant, and other additives may also be appropriately used, as desired, in polymerization.

The atmosphere in the polymerization reaction is not limited, and the polymerization may be performed in the ambient air, or under an atmosphere of an inert gas, such as nitrogen gas or argon gas. The reaction liquid may be stirred in the polymerization reaction.

The copolymer may precipitate in the polymerization reaction. The copolymer after polymerization can be purified by a common purification method, such as reprecipitation, dialysis, ultrafiltration, or extraction.

The copolymer after purification may be dried by any method, such as lyophilization, vacuum drying, spray drying, or heat drying, but from the viewpoint of small influence on the physical properties of the polymer, lyophilization or vacuum drying is exemplary.

The proportion of the structural units derived from each polymerizable monomer in the obtained copolymer can be determined by analyzing peak intensities of groups contained in the structural units using any suitable means such as NMR or IR.

The amount of unreacted monomers contained in the obtained copolymer can be 0.01% by weight or less based on the entire copolymer. A smaller amount of unreacted monomers is exemplary. For example, the amount of unreacted monomers can be 0% by weight based on the entire copolymer. The content of remaining monomers can be measured by any suitable means, for example, high performance liquid chromatography.

<Medical Device>

The present disclosure also provides a medical device including a substrate layer and a surface lubricious layer that is formed on at least a part of the surface of the substrate layer and that contains the hydrophilic copolymer.

An exemplary embodiment of the medical device will be described below with reference to the accompanying drawings.

FIG. 1 is a partial cross sectional view schematically illustrating a surface lamination structure of an exemplary embodiment of a medical device. FIG. 2 is a partial cross sectional view schematically illustrating a different configuration example of a surface lamination structure. In FIG. 1 and FIG. 2, 1 denotes a substrate layer, 1a denotes a substrate layer core, 1b denotes a substrate surface layer, 2 denotes a surface lubricious layer, and 10 denotes a medical device.

As shown in FIG. 1 and FIG. 2, a medical device 10 includes a substrate layer 1 and a surface lubricious layer 2 that is fixed on at least a part of the substrate layer 1 (the figures show an example in which the surface lubricious layer 2 is fixed on all of the surface (the entire surface) of the substrate layer 1 in the figures) and that contains a hydrophilic copolymer. The surface lubricious layer 2 binds to the substrate layer 1 via a photoreactive group of the hydrophilic copolymer.

The components of the exemplary medical device will be described below.

[Substrate Layer (Substrate)]

The substrate layer may be constituted of any material that can react with a photoreactive group contained in the hydrophilic copolymer to form a chemical bond. Examples of materials for constituting or forming the substrate layer 1 include metal materials, polymer materials, and ceramics. Regarding the substrate layer 1, the entire substrate layer 1 (all of the substrate layer 1) may be constituted or formed of any one of the materials as shown in FIG. 1, or the substrate layer 1 may have a structure in which the surface of the substrate layer core 1a which is constituted or formed of any one of the materials is covered or coated with another one of the materials by a suitable method to constitute or form a substrate surface layer 1b as shown in FIG. 2. Examples of the latter cases include a case where the surface of the substrate layer core 1a formed of a resin material and the like is covered or coated with a metal material by a suitable method (for example, plating, metal vapor deposition, or sputtering) to form the substrate surface layer 1b; and a case where the surface of the substrate layer core 1a formed of a hard reinforcing material, such as a metal material or a ceramic material, is covered or coated with a polymer material which is softer than a reinforcing material, such as metal material, by a suitable method (for example, dipping, spray, or application/printing), or a reinforcing material of the substrate layer core 1a and a polymer material of the substrate surface layer 1b are combined into a composite (for example, with a suitable reaction treatment), to form the substrate surface layer 1b. The substrate layer core 1a may be a multilayer structure in which multiple different materials are laminated, or a structure in which members formed of different materials for the respective parts of a medical device are joined. Another layer, i.e., a middle layer (not shown) may further be formed between the substrate layer core 1a and the substrate surface layer 1b. The substrate surface layer 1b may also be a multilayer structure in which multiple different materials are laminated or a structure in which members formed of different materials for the respective parts of a medical device are joined.

Among the materials constituting or forming the substrate layer 1, the metal material is not limited and metal materials that are suitable for use in medical devices, such as catheters, stents, and guide wires can be used. Examples include a stainless steel (SUS), such as SUS304, SUS316, SUS316L, SUS420J2, and SUS630, gold, platinum, silver, copper, nickel, cobalt, titanium, iron, aluminum, tin, and various alloys, such as nickel-titanium (Ni—Ti) alloys, nickel-cobalt (Ni—Co) alloys, cobalt-chromium (Co—Cr) alloys, and zinc-tungsten (Zn—W) alloys. One of the metal materials may be used alone or two or more thereof may be used in combination. The metal material may be appropriately selected to be most suitable for the substrate layer of a catheter, stent, guide wire, or the like, which is the use target.

Among the materials constituting or forming the substrate layer 1, the polymer material is not limited and polymer materials that are suitable for use in medical devices, such as catheters, stents, and guide wires can be used. Examples include polyamide resins, polyolefin resins, such as polyethylenes, for example, straight chain low density polyethylenes (LLDPE), low density polyethylenes (LDPE), and high density polyethylenes (HDPE), and polypropylene, and polyester resins, such as polyethylene terephthalate, styrol resins, such as polystyrene, cyclic polyolefin resins, modified polyolefin resins, epoxy resins, urethane resins, diallylphthalate resins (allyl resins), polycarbonate resins, fluororesins, amino resins (urea resins, melamine resins, benzoguanamine resins), acrylic resins, polyacetal resins, vinyl acetate resins, phenol resins, vinyl chloride resins, silicone resins (silicon resins), polyether resins, and polyimide resins. One of the polymer materials may be used alone or two or more thereof may be used in combination. The polymer material may be appropriately selected to be most suitable for the substrate layer of a catheter, stent, guide wire, or the like, which is the use target.

The shape of the substrate layer is not limited and can be appropriately selected, for example, according to the use form, such as a sheet form, a liner form (wire), or a tubular form.

[Method of Producing Medical Device]

The method of producing the medical device is not limited. The method of forming the surface lubricious layer on a substrate layer is not limited. For example, the method uses the hydrophilic copolymer, and any suitable method may be applied as it is or with appropriate modification. For example, the hydrophilic copolymer can be dissolved in a solvent to prepare a coating liquid, which is then applied on a substrate layer of a medical device. For example, lubricating property and durability (lubrication retaining property) can be imparted to a surface of a medical device.

(Application Step)

In an exemplary method, as a solvent used for dissolving the hydrophilic copolymer, solvents described in the section [Physical properties of hydrophilic copolymer] can be used from the viewpoint of safety of the operation (for example, low toxicity).

The concentration of the hydrophilic copolymer in the coating liquid can be, but is not limited to, 0.01 to 50% by weight, for example, 0.05 to 40% by weight, for example, 0.1 to 30% by weight. For example, in the range, applicability of the coating liquid can be good and the obtained surface lubricious layer can be superior in the lubricating property and durability (lubrication retaining property). In addition, since a uniform surface lubricious layer having a desired thickness can be easily obtained through a single coating, such a concentration is exemplary in terms of production efficiency. For example, when the concentration of the hydrophilic copolymer is less than 0.01% by weight, a sufficient amount of the hydrophilic copolymer may not be fixed on a substrate layer surface. For example, when the concentration of the hydrophilic copolymer exceeds 30% by weight, the viscosity of the coating liquid may be so high that a surface lubricious layer having a uniform thickness may not be obtained. However, a concentration outside the range may be sufficiently applicable to the extent that the exemplary functions and effects of the present disclosure are not influenced.

The substrate layer surface may be previously subjected to a UV irradiation treatment, a plasma treatment, a corona discharge treatment, a flame treatment, an oxidation treatment, a silane coupling treatment, or a phosphate coupling treatment before application of a coating liquid. When the solvent of a coating liquid is only water, it can be difficult to apply the coating liquid on a hydrophobic substrate layer surface. However, a plasma treatment of the substrate layer surface hydrophilizes the substrate layer surface. This can lead to enhancement of wettability of a coating liquid to a substrate layer surface, making it possible to form a uniform surface lubricious layer. In addition, application of the treatments on a substrate layer surface of a material having no C—H bond, such as a metal or a fluororesin, makes it possible to form a covalent bond to the photoreactive group of the hydrophilic copolymer.

The method of applying a coating liquid to a substrate layer surface is not limited, and any suitable method, such as an application/printing method, a dipping or dip-coating method, a spraying method, a spin coating method, or a mixed solution-impregnated sponge coating method can be applied. Among them, a dipping or dip-coating method is exemplary.

For example, when a surface lubricious layer is to be formed on a thin and narrow interior surface of a catheter, a stent, a guide wire, or the like, the pressure of the system may be reduced for degassing while dipping the substrate layer in a coating liquid. Degassing by reducing the pressure can allow a solution to quickly permeate the thin and narrow interior surface to facilitate the formation of the surface lubricious layer.

For example, when the surface lubricious layer is to be formed on only a part of a substrate layer, only a part of the substrate layer is dipped in a coating liquid to coat the part of the substrate layer with the coating liquid. A surface lubricious layer can thus be formed on a desired surface part of a substrate layer.

For example, when it is difficult to dip only a part of a substrate layer in a coating liquid, a part of the substrate layer surface where a surface lubricious layer is not required to be formed is protected (for example, covered) with a suitable removable or detachable member or material. Then, the substrate layer can be dipped in a coating liquid to coat the substrate layer with the coating liquid. Thereafter, the protecting member (material) on the part of the substrate layer surface where a surface lubricious layer is not required to be formed can be removed, followed by a reaction through a heating operation or the like. In this exemplary manner, a surface lubricious layer can be formed on a desired part of a substrate layer surface. However, the present disclosure is not limited to the above formation methods, and any suitable method can be appropriately used to form a surface lubricious layer. For example, when it is difficult to dip only a part of a substrate layer in a mixed solution, in place of a dipping method, another coating method (for example, a method of applying a coating liquid to a desired part of a surface of a medical device with an applicator, such as a spray apparatus, a bar coater, a die coater, a reverse coater, a comma coater, a gravure coater, a spray coater, or a doctor knife) may be applied. For example, when both of the outer surface and the inner surface of a cylindrical medical device are desired to have a surface lubricious layer due to the structure of the medical device, a dipping method can be used since both the outer surface and the inner surface can be coated at once.

(Drying Step)

For example, a substrate layer can be dipped in a coating liquid containing the hydrophilic copolymer as described above. Then, the substrate layer can be taken out of the coating liquid, and the coating film can be dried. The drying conditions are not limited. The drying conditions can remove the solvent from the coating film. For example, a hot air treatment with a dryer or the like or a natural drying may be used. The pressure condition in drying is also not limited.

The drying may be performed at normal pressure (the atmospheric pressure), or at an increased or decreased pressure. As a drying means (such as a device), for example, an oven or a vacuum dryer may be used. In the case of natural drying, no drying device is needed.

(Fixing Step)

For example, the coating film after the drying step can be irradiated with an active energy ray. This can activate the photoreactive group of the hydrophilic copolymer in the coating film to form a chemical bond between the photoreactive group and the substrate layer. An exemplary description is provided for a case of combination of a photoreactive group having a benzophenone structure and a polyethylene substrate layer. For example, when the hydrophilic copolymer contains a photoreactive group having a benzophenone structure, two radicals are generated in the photoreactive group by irradiation with a UV ray. One radical thereof withdraws a hydrogen atom from the polyethylene substrate layer, and instead, one radical is generated on the polyethylene substrate layer. Then, the remaining radical in the photoreactive group is bound to the radical on the polyethylene substrate layer to thereby form a covalent bond between the photoreactive group and the polyethylene substrate layer. This exemplary mechanism can allow the surface lubricious layer containing the hydrophilic copolymer having a photoreactive group to be strongly fixed to the substrate layer surface. Thus, the surface lubricious layer can exhibit superior durability (lubrication retaining property).

Examples of active energy rays include UV rays, electron rays, and gamma rays. The active energy ray can be a UV ray or an electron ray, and in view of influence on human bodies, it can be a UV ray. When a UV ray is used, any wavelength that can activate a photoreactive group can be appropriately selected as the irradiation wavelength. The irradiation intensity of the UV ray can be, but is not limited to, 1 to 5000 mW/cm$^2$. The integrated light quantity of the UV ray can be, but is not limited to, 50 to 5000 mJ/cm$^2$, for example, 100 to 1000 mJ/cm$^2$. Examples of the device for the UV ray irradiation include high pressure mercury lamps, low pressure mercury lamps, metal halide lamps, xenon lamps, and halogen lamps.

After the irradiation with the active energy ray, the substrate layer surface may be washed with a solvent (for example, a solvent used in preparing a coating liquid) to remove the unreacted hydrophilic copolymer.

The fixation of the coating film (surface lubricious layer) onto the substrate layer can be checked using an analysis means, such as FT-IR or XPS. For example, the fixation can be checked by comparing the ratio of a peak of a bond formed through the irradiation with the active energy ray and a peak of an unchanged bond using FT-IR measurement before and after the irradiation with an active energy ray.

In an exemplary medical device, a surface lubricious layer containing the hydrophilic copolymer is formed on a surface. Thus, an exemplary medical device can exhibit superior lubricating property and durability (lubrication retaining property).

[Use of Medical Device]

The medical device 10 can be used in contact with body fluid or blood. The surface can have a lubricating property in an aqueous solution such as body fluid or a saline, being capable of enhancing operability and reducing damage of tissue mucosa. Examples include catheters, stents, and guide wires which are used in blood vessels. For example, the medical device having a surface lubricious layer containing the hydrophilic copolymer can be a catheter, a stent, or a guide wire. For example, the medical device can include:

(a) Catheters to be orally or nasally inserted or allowed to indwell in a digestive organ, such as stomach tube catheters, digestive catheters, and tubes for enteric nutrients;

(b) Catheters to be orally or nasally inserted or allowed to indwell in a respiratory tract or trachea, such as oxygen catheters, oxygen cannulas, tubes and cuffs of tracheal tubes, tubes and cuffs of tracheotomy tubes, and tracheal aspiration catheters;

(c) Catheters to be inserted or allowed to indwell in a urethra or ureter, such as urethra catheters, urinary catheters, and catheters and balloons of urethra balloon catheters;

(d) Catheters to be inserted or allowed to indwell in various lumens, organs, and tissues, such as suction catheters, drain catheters, and rectum catheters;

(e) Catheters to be inserted or allowed to indwell in a blood vessel, such as indwelling needles, IVH catheters, thermodilution catheters, angiography catheters, vasodilation catheters, and dilators or introducers, or guide wires, stylets, and the like for the catheters;

(f) Artificial tracheae, artificial bronchi, and the like;

(g) Medical devices for extracorporeal circulation therapy (artificial lungs, artificial hearts, artificial kidneys, etc.) and circuits therefor.

Exemplary aspects of the present disclosure will be described specifically below with respect to examples, but the present disclosure is not to be limited to the examples. Note that the parts and % in the examples are all by weight. In the examples, unless otherwise defined, the conditions for allowing to stand at room temperature are all at 23° C./55% RH.

Production of Copolymer

Production Example 1

In 10 mL of a methanol/water (9/1 v/v) mixed solvent were dissolved 1.95 g (7.0 mmol) of [2-(methacryloyloxy)ethyl]dimethyl-(3-sulfopropyl)ammonium hydroxide (MSPB) from Sigma-Aldrich, 0.410 g (2.0 mmol) of 2-acrylamide-2-methyl-1-propanesulfonic acid (AMPS) from Tokyo Chemical Industry, Co., Ltd., and 0.266 g (1.0 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 31 mg (0.10 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation, and the obtained insoluble matter was dissolved in 1 mL of a methanol/water (7/3 v/v) mixed solvent. The solution was subjected to reprecipitation in acetone, and the supernatant was removed by decantation, followed by washing twice with methanol, to obtain a copolymer.

Production Example 2

In 1 mL of a methanol/water (9/1 v/v) mixed solvent were dissolved 0.251 g (0.9 mmol) of [2-(methacryloyloxy)ethyl]dimethyl-(3-sulfopropyl)ammonium hydroxide (MSPB) from Sigma-Aldrich and 0.027 g (0.1 mmol) of 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 3

In 1 mL of a methanol/water (9/1 v/v) mixed solvent were dissolved 0.276 g (0.99 mmol) of [2-(methacryloyloxy)ethyl]dimethyl-(3-sulfopropyl)ammonium hydroxide (MSPB) from Sigma-Aldrich and 0.003 g (0.01 mmol) 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 4

In 1 mL of methanol were dissolved 0.167 g (0.6 mmol) of [2-(methacryloyloxy)ethyl]dimethyl-(3-sulfopropyl)ammonium hydroxide (MSPB) from Sigma-Aldrich, 0.043 g (0.3 mmol) of butyl methacrylate (BMA) from Tokyo Chemical Industry, Co., Ltd., and 0.027 g (0.1 mmol) of 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 5

In 1 mL of methanol were dissolved 0.167 g (0.6 mmol) of [2-(methacryloyloxy)ethyl]dimethyl-(3-sulfopropyl)ammonium hydroxide (MSPB) from Sigma-Aldrich, 0.039 g (0.3 mmol) of 2-methoxyethyl acrylate (MEA) from Wako Pure Chemical Corporation, and 0.027 g (0.1 mmol) of 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 6

In 1 mL of methanol were dissolved 0.167 g (0.6 mmol) of [2-(methacryloyloxy)ethyl]dimethyl-(3-sulfopropyl)ammonium hydroxide (MSPB) from Sigma-Aldrich, 0.034 g (0.3 mmol) of N-isopropylacrylamide (NIPAAm) from Wako Pure Chemical Corporation, and 0.027 g (0.1 mmol) of 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 7

In 1 mL of methanol were dissolved 0.167 g (0.6 mmol) of [2-(methacryloyloxy)ethyl]dimethyl-(3-sulfopropyl)ammonium hydroxide (MSPB) from Sigma-Aldrich, 0.030 g (0.3 mmol) of N,N-dimethylacrylamide (DMAAm) from Tokyo Chemical Industry, Co., Ltd., and 0.027 g (0.1 mmol) of 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 8

In 1 mL of methanol were dissolved 0.167 g (0.6 mmol) of [2-(methacryloyloxy)ethyl]dimethyl-(3-sulfopropyl)ammonium hydroxide (MSPB) from Sigma-Aldrich, 0.090 g (0.3 mmol) of poly(ethylene glycol) methyl ether methacrylate (PEGMEA, number average molecular weight 300) from Sigma-Aldrich, and 0.027 g (0.1 mmol) of 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 9

In 1 mL of methanol were dissolved 0.167 g (0.6 mmol) of [2-(methacryloyloxy)ethyl]dimethyl-(3-sulfopropyl)ammonium hydroxide (MSPB) from Sigma-Aldrich, 0.035 g (0.3 mmol) of N-(2-hydroxyethyl)acrylamide (HEAAm) from Tokyo Chemical Industry, Co., Ltd., and 0.027 g (0.1 mmol) of 4-methacryloyloxybenzophenone (MBP) from MRC UNITEC Co., Ltd. to prepare a reaction solution. Next, the reaction solution was put in a 15 mL centrifuge tube, oxygen was removed by sufficient nitrogen bubbling, 3.1 mg (0.01 mmol) of a polymerization initiator, 2,2'-azobis(4-methoxy-2,4-dimethylvaleronitrile) was added, followed by immediate sealing, and polymerization was carried out in a water bath at 50° C. for 2 hours. As the polymerization proceeded, insoluble matter precipitated and settled down. Next, the solvent was removed by decantation to obtain the insoluble matter (copolymer).

Production Example 10

In 10 mL of a methanol/water (9/1 v/v) mixed solvent were dissolved 2.07 g (7.0 mmol) of 2-methacryloyloxyethyl phosphorylcholine (MPC) from Tokyo Chemical Industry, Co., Ltd., 0.414 g (2.0 mmol) of 2-acrylamide-2-methyl-1-propanesulfonic acid (AMPS) from Tokyo Chemical Industry, Co., Ltd., and 0.266 g (1.0 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 31 mg (0.10 mmol) of a polymerization initiator, 2,2'-azobis(4-methoxy-2,4-dimethylvaleronitrile) was added, followed by immediate sealing, and polymerization was carried out in a water bath at 50° C. for 2 hours. Next, the obtained polymerization liquid was subjected to reprecipitation in the 5-fold amount of THF/methanol (9/1 v/v), and the supernatant was removed by decantation, followed by washing twice with THF/methanol (9/1 v/v), to obtain a copolymer.

Production Example 11

In 10 mL of a 2,2,2-trifluoroethanol/water (9/1 v/v) mixed solvent were dissolved 1.95 g (7.0 mmol) of [3-(methacryloylamino)propyl]dimethyl(3-sulfopropyl)ammonium hydroxide (MSPBa) from Sigma-Aldrich, 0.580 g (2.8 mmol) of 2-acrylamide-2-methyl-1-propanesulfonic acid (AMPS) from Tokyo Chemical Industry, Co., Ltd., and 0.053 g (0.2 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 12

In 10 mL of a 2,2,2-trifluoroethanol/water (9/1 v/v) mixed solvent were dissolved 2.07 g (7.0 mmol) of 2-methacryloyloxyethyl phosphorylcholine (MPC) from Tokyo Chemical Industry, Co., Ltd., 0.580 g (2.8 mmol) of 2-acrylamide-2-methyl-1-propanesulfonic acid (AMPS) from Tokyo Chemical Industry, Co., Ltd., and 0.053 g (0.2 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 13

In 10 mL of a 2,2,2-trifluoroethanol/water (9/1 v/v) mixed solvent were dissolved 1.95 g (7.0 mmol) of [2-(methacryloyloxy)ethyl]dimethyl-(3-sulfopropyl)ammonium hydroxide (MSPB) from Sigma-Aldrich, 0.580 g (2.8 mmol) of 2-acrylamide-2-methyl-1-propanesulfonic acid (AMPS) from Tokyo Chemical Industry, Co., Ltd., and 0.053 g (0.2 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 14

In 10 mL of a 2,2,2-trifluoroethanol/water (8/2 v/v) mixed solvent were dissolved 2.76 g (9.89 mmol) of [2-(methacryloyloxy)ethyl]dimethyl-(3-sulfopropyl)ammonium hydroxide (MSPB) from Sigma-Aldrich, 0.023 g (0.1 mmol) 2-acrylamide-2-methyl-1-propanesulfonic acid sodium salt (AMPS(Na)) from Sigma-Aldrich, and 0.003 g (0.01 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 15

In 10 mL of a 2,2,2-trifluoroethanol/water (8/2 v/v) mixed solvent were dissolved 1.96 g (7.0 mmol) of [2-(methacryloyloxy)ethyl]dimethyl-(3-sulfopropyl)ammonium hydroxide (MSPB) from Sigma-Aldrich, 0.458 g (2.0 mmol) of 2-acrylamide-2-methyl-1-propanesulfonic acid sodium salt (AMPS(Na)) from Sigma-Aldrich, and 0.266 g (1.0 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 16

In 10 mL of a 2,2,2-trifluoroethanol/water (8/2 v/v) mixed solvent were dissolved 1.68 g (6.0 mmol) [2-(methacryloyloxy)ethyl]dimethyl-(3-sulfopropyl)ammonium hydroxide (MSPB) from Sigma-Aldrich, 0.458 g (2.0 mmol) of 2-acrylamide-2-methyl-1-propanesulfonic acid sodium salt (AMPS(Na)) from Sigma-Aldrich, and 0.532 g (2.0 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 17

In 10 mL of a 2,2,2-trifluoroethanol/water (9/1 v/v) mixed solvent were dissolved 0.003 g (0.01 mmol) of [2-(methacryloyloxy)ethyl]dimethyl-(3-sulfopropyl)ammonium hydroxide (MSPB) from Sigma-Aldrich, 2.05 g (9.89 mmol) of 2-acrylamide-2-methyl-1-propanesulfonic acid (AMPS) from Tokyo Chemical Industry, Co., Ltd., and 0.027 g (0.1 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 18

In 10 mL of a 2,2,2-trifluoroethanol/water (8/2 v/v) mixed solvent were dissolved 1.96 g (7.0 mmol) of [2-(methacryloyloxy)ethyl]dimethyl-(3-sulfopropyl)ammonium hydroxide (MSPB) from Sigma-Aldrich, 0.685 g (2.99 mmol) of 2-acrylamide-2-methyl-1-propanesulfonic acid sodium salt (AMPS(Na)) from Sigma-Aldrich, and 0.003 g (0.01 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 19

In 10 mL of a 2,2,2-trifluoroethanol/water (8/2 v/v) mixed solvent were dissolved 1.96 g (7.0 mmol) of [2-(methacryloyloxy)ethyl]dimethyl-(3-sulfopropyl)ammonium hydroxide (MSPB) from Sigma-Aldrich, 0.465 g (2.0 mmol) of 3-sulfopropylacrylate potassium salt (SPA(K)) form Tokyo Chemical Industry, Co., Ltd., and 0.266 g (1.0 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

Production Example 20

In 10 mL of a 2,2,2-trifluoroethanol/water (8/2 v/v) mixed solvent were dissolved 1.96 g (7.0 mmol) of [2-(methacryloyloxy)ethyl]dimethyl-(3-sulfopropyl)ammonium hydroxide (MSPB) from Sigma-Aldrich, 0.493 g (2.0 mmol) of 3-sulfopropylmethacrylate potassium salt (SPMA(K)) from Sigma-Aldrich, and 0.266 g (1.0 mmol) of 4-methacryloyloxybenzophenone (MBP) from MRC UNITEC Co., Ltd. to prepare a reaction solution. Next, the reaction solution was put in a 30 mL eggplant-shaped flask, oxygen was removed by sufficient nitrogen bubbling, 28 mg (0.10 mmol) of a polymerization initiator (V-501 from Wako Pure Chemical Corporation) was added, followed by immediate sealing, and polymerization was carried out in a water bath at 80° C. for 2 hours. Next, reprecipitation was performed in acetone, and the supernatant was removed by decantation, followed by washing twice with methanol, to obtain a copolymer.

The compositions of the copolymers obtained in the Production Examples 1 to 20 were shown in Table 1-1 and Table 1-2. Here, the copolymers of Production Examples 1, 11, and 13 to 20 correspond to the hydrophilic copolymer according to the present disclosure, and the copolymers of Production Examples 10 and 12 correspond to the copolymer disclosed in ACS Appl. Mater. Interface, 2015, 7(31), pp. 17489-17498.

TABLE 1-1

| | Structural unit ratio (% by mole) | | | | | | | | | |
|---|---|---|---|---|---|---|---|---|---|---|
| | MSPB | MPC | AMPS | BMA | MEA | NIPAAm | DMAAm | PEGMA | HEAAm | MBP |
| Production Example 1 | 70 | | 20 | | | | | | | 10 |
| Production Example 2 | 90 | | | | | | | | | 10 |
| Production Example 3 | 99 | | | | | | | | | 1 |
| Production Example 4 | 60 | | | 30 | | | | | | 10 |
| Production Example 5 | 60 | | | | 30 | | | | | 10 |
| Production Example 6 | 60 | | | | | 30 | | | | 10 |
| Production Example 7 | 60 | | | | | | 30 | | | 10 |
| Production Example 8 | 60 | | | | | | | 30 | | 10 |
| Production Example 9 | 60 | | | | | | | | 30 | 10 |
| Production Example 10 | | 70 | 20 | | | | | | | 10 |

TABLE 1-2

| | Structural unit ratio (% by mole) | | | | | | | |
|---|---|---|---|---|---|---|---|---|
| | MSPB | MSPBa | MPC | AMPS | AMPS (Na) | SPA (K) | SPMA (K) | MBP |
| Production Example 11 | | 70 | | 28 | | | | 2 |
| Production Example 12 | | | 70 | 28 | | | | 2 |
| Production Example 13 | 70 | | | 28 | | | | 2 |
| Production Example 14 | 98.9 | | | | 1 | | | 0.1 |
| Production Example 15 | 70 | | | | 20 | | | 10 |
| Production Example 16 | 60 | | | | 20 | | | 20 |
| Production Example 17 | 0.1 | | | 98.9 | | | | 1 |
| Production Example 18 | 70 | | | | 29.9 | | | 0.1 |
| Production Example 19 | 70 | | | | | 20 | | 10 |
| Production Example 20 | 70 | | | | | | 20 | 10 |

In Table 1-1 and Table 1-2, the abbreviations represent the followings:

MSPB: [2-(methacryloyloxy)ethyl]dimethyl-(3-sulfopropyl)ammonium hydroxide (corresponding to monomer A)

MSPBa: [3-(methacryloylamino)propyl]dimethyl(3-sulfopropyl)ammonium hydroxide (corresponding to monomer A)

MPC: 2-methacryloyloxyethyl phosphorylcholine

AMPS: 2-acrylamide-2-methyl-1-propanesulfonic acid (corresponding to monomer B)

AMPS(Na): 2-acrylamide-2-methyl-1-propanesulfonic acid sodium salt (corresponding to monomer B)

SPA(K): 3-sulfopropylacrylate potassium salt (corresponding to monomer B)

SPMA(K): 3-sulfopropylmethacrylate potassium salt (corresponding to monomer B)

BMA: butyl methacrylate

MEA: 2-methoxyethyl acrylate

NIPAAm: N-isopropylacrylamide

DMAAm: N,N-dimethylacrylamide

PEGMA: poly(ethylene glycol) methyl ether methacrylate

HEAAm: N-(2-hydroxyethyl)acrylamide

MBP: 4-methacryloyloxybenzophenone (corresponding to monomer C).

Solvent Solubility Test of Copolymer

Examples 1-1 to 10-1, Comparative Examples 1-1 to 10-1

The copolymers obtained in Production Examples 1 to 20 were evaluated for the solubility in water, methanol, and water/methanol mixed solvents having different mixing ratios. Specifically, solubility tests were performed under conditions of a temperature of 25° C., a concentration of 1% by weight, and a testing time of 2 hours, and the solubility was determined according to the following determination criteria:

○: the copolymer dissolved or dispersed x: the copolymer did not dissolve or disperse.

The results are shown in Table 2. The copolymers of Production Examples 1, 11, and 13 to 20 (corresponding to an exemplary hydrophilic copolymer according to the present disclosure) showed good solubility in water or water/methanol mixed solvents (Examples 1-1 to 10-1). On the other hand, the copolymers of Production Examples 2 to 9, which contained no structural unit derived from the monomer B (AMPS) did not dissolve in water/methanol solvents of any mixing ratios (Comparative Examples 1-1 to 8-1). Based on the results, it is considered that the structural unit derived from the monomer B contributes to the solvent solubility of the copolymers. Without being bound to any particular theory, this is supposedly because the electrostatic repulsion between sulfonic acid groups contained in the structural units derived from the monomer B possibly contributes to dispersion of the copolymer. The copolymer of Production Examples 10 and 12 (corresponding to the copolymer disclosed in ACS Appl. Mater. Interface, 2015, 7(31), pp. 17489-17498) showed solubility in water/methanol of any mixing ratio (Comparative Example 9-1, Comparative Example 10-1).

TABLE 2

| | | Solubility or dispersibility in water/methanol (v/v) | | | | | | |
|---|---|---|---|---|---|---|---|---|
| | Production Example | 10/0 | 9/1 | 7/3 | 5/5 | 3/7 | 1/9 | 0/10 |
| Example 1-1 | Production Example 1 | ○ | ○ | ○ | ○ | ○ | x | x |
| Comparative Example 1-1 | Production Example 2 | x | x | x | x | x | x | x |
| Comparative Example 2-1 | Production Example 3 | x | x | x | x | x | x | x |
| Comparative Example 3-1 | Production Example 4 | x | x | x | x | x | x | x |
| Comparative Example 4-1 | Production Example 5 | x | x | x | x | x | x | x |
| Comparative Example 5-1 | Production Example 6 | x | x | x | x | x | x | x |
| Comparative Example 6-1 | Production Example 7 | x | x | x | x | x | x | x |
| Comparative Example 7-1 | Production Example 8 | x | x | x | x | x | x | x |
| Comparative Example 8-1 | Production Example 9 | x | x | x | x | x | x | x |
| Comparative Example 9-1 | Production Example 10 | ○ | ○ | ○ | ○ | ○ | ○ | ○ |
| Example 2-1 | Production Example 11 | ○ | ○ | ○ | ○ | ○ | x | x |
| Comparative Example 10-1 | Production Example 12 | ○ | ○ | ○ | ○ | ○ | ○ | ○ |
| Example 3-1 | Production Example 13 | ○ | ○ | ○ | ○ | ○ | x | x |
| Example 4-1 | Production Example 14 | ○ | x | x | x | x | x | x |
| Example 5-1 | Production Example 15 | ○ | ○ | ○ | ○ | ○ | x | x |
| Example 6-1 | Production Example 16 | x | x | x | x | ○ | x | x |
| Example 7-1 | Production Example 17 | ○ | ○ | ○ | ○ | ○ | ○ | ○ |
| Example 8-1 | Production Example 18 | ○ | ○ | ○ | ○ | x | x | x |
| Example 9-1 | Production Example 19 | ○ | ○ | ○ | ○ | x | x | x |
| Example 10-1 | Production Example 20 | ○ | ○ | ○ | ○ | x | x | x |

Slide and Durability Test

Example 1-2

The copolymer obtained in Production Example 1 (corresponding to an exemplary hydrophilic copolymer according to the present disclosure) was dissolved in methanol/water (7/3 v/v) at 10% by weight to prepare a coating liquid. Next, an HDPE sheet (12.5 mm ϕ100 mm) was dipped in the coating liquid and was taken out at a speed of 15 mm/sec. Next, the HDPE sheet was dried with a dryer for 30 seconds to remove the solvent. Next, the HDPE sheet was irradiated with UV under conditions of a wavelength of 365 nm, a lamp power of 1 kW, an irradiation distance of 200 mm, and a sample transporting rate of 2 m/min (integrated light quantity: 230 mJ/cm$^2$). UVC-1212/1MNLC3-AA04 (high pressure mercury lamp) manufactured by Ushio Inc. was used as a UV irradiation device.

Next, the obtained sample was evaluated for the lubricating property and durability (lubrication retaining property) using a friction meter (Handy Tribo Master TL201 manufactured by Trinity-Lab Inc.) 20 shown in FIG. 3 according to the following method.

That is, the sample 16 was fixed in a petri dish 12, and was dipped in water 17 with such a height that the entire sample 16 soaked therein. The petri dish 12 was placed on a moving table 15 of the friction meter 20 illustrated in FIG. 3. An HDPE terminal (φ 10 mm, R 1 mm) 13 was brought into contact with the sheet, and a load 14 of 450 g was applied on the terminal. While the moving table 15 was subjected to 50 horizontal reciprocations under a sliding distance set to 20 mm and a sliding speed set to 16.7 mm/sec, the sliding resistance (gf) was measured. During the reciprocations from the first time to 50th time, an average of the sliding resistance for each reciprocation was taken and plotted on a graph as a test force to thereby evaluate the variation of the sliding resistance during the 50 repeated slides.

Example 3-2

The copolymer obtained in Production Example 13 (corresponding to an exemplary hydrophilic copolymer according to the present disclosure) was dissolved in methanol/water (7/3 v/v) at 10% by weight to prepare a coating liquid. Next, a nylon sheet (12.5 mm×100 mm) was dipped in the coating liquid and was taken out at a speed of 5 mm/sec. Next, the nylon sheet was dried with a dryer for 30 seconds to remove the solvent. Next, the nylon sheet was irradiated with UV under conditions of a wavelength of 365 nm, a lamp power of 1 kW, an irradiation distance of 200 mm, and a sample transporting rate of 250 m/min (integrated light quantity: 1000 mJ/cm$^2$). UVC-1212/1MNLC3-AA04 (high pressure mercury lamp) manufactured by Ushio Inc. was used as a UV irradiation device.

Next, the obtained sample was evaluated for the lubricating property and durability (lubrication retaining property) using a friction meter (Handy Tribo Master TL201 manufactured by Trinity-Lab Inc.) 20 shown in FIG. 3 according to the following method That is, the sample 16 was fixed in a petri dish 12, and was dipped in water 17 with such a height that the entire sample 16 soaked therein. The petri dish 12 was placed on a moving table 15 of the friction meter 20 illustrated in FIG. 3. An HDPE terminal (φ 10 mm, R 1 mm) 13 was brought into contact with the sheet, and a load 14 of 450 g was applied on the terminal. While the moving table 15 was subjected to 50 horizontal reciprocations under a sliding distance set to 20 mm and a set sliding speed of 16.7 mm/sec, the sliding resistance (gf) was measured. During the reciprocations from the first time to 50th time, an average of the sliding resistance for each reciprocation was taken and plotted on a graph as a test force to thereby evaluate the variation of the sliding resistance during the sliding repeated 100 times.

Example 5-2

Production of the sample and measurement of sliding resistance were performed in the same manner as in Example 3-2 except for using the copolymer obtained in Production Example 15 in place of the copolymer obtained in Production Example 13.

Example 7-2

Production of the sample and measurement of sliding resistance were performed in the same manner as in Example 3-2 except for using the copolymer obtained in Production Example 17 in place of the copolymer obtained in Production Example 13.

Comparative Example 9-2

Production of the sample and measurement of sliding resistance were performed in the same manner as in Example 1-2 except for using the copolymer obtained in Production Example 10 (corresponding to the copolymer disclosed in ACS Appl. Mater. Interface, 2015, 7(31), pp. 17489-17498) in place of the copolymer obtained in Production Example 1.

The results of Example 1-2 and Comparative Example 9-2 are shown in FIG. 4. The sample of Example 1-2 had a significantly lower initial sliding value as compared with the sample of Comparative Example 9-2. The sliding resistance of the sample of Comparative Example 9-2 increases from 0 to 10th sliding, which suggests the possibility of wear of the surface of the surface lubricious layer. On the other hand, the sample of Example 1-2 did not present such a phenomenon that the sliding resistance increases as the sliding time increases. The above fact indicates that the surface lubricious layer formed using the exemplary hydrophilic copolymer according to the present disclosure has higher film strength as compared with the surface lubricious layer formed using the copolymer disclosed in ACS Appl. Mater. Interface, 2015, 7(31), pp. 17489-17498. Without being bound by any particular theory, this may be attributable to the strong electrostatic interaction of the sulfobetaine structure.

It was found from the above results that the surface lubricious layer containing the exemplary hydrophilic copolymer according to the present disclosure can exhibit superior lubricating property and durability (lubrication retaining property).

Comparative Example 10-2

Production of the sample and measurement of sliding resistance were performed in the same manner as in Example 3-2 except for using the copolymer obtained in Production Example 12 (corresponding to the copolymer disclosed in ACS Appl. Mater. Interface, 2015, 7(31), pp. 17489-17498) in place of the copolymer obtained in Production Example 13.

The results of Example 3-2, Example 5-2, Example 7-2, and Comparative Example 10-2 are shown in FIG. 5. The samples of Example 3-2, Example 5-2, and Example 7-2 had significantly low initial sliding values as compared with the sample of Comparative Example 10-2. Based on the above, it is considered that the surface lubricious layer formed using the exemplary hydrophilic copolymer according to the present disclosure has superior slidability and durability as compared with the surface lubricious layer formed using the copolymer disclosed in ACS Appl. Mater. Interface, 2015, 7(31), pp. 17489-17498.

It was found from the above results that the surface lubricious layer containing the hydrophilic copolymer according to the present disclosure can exhibit superior lubricating property and durability (lubrication retaining property).

The present application is based on Japanese Patent Application No. 2016-164815 filed on Aug. 25, 2016, and the entire disclosure is incorporated herein by reference.

What is claimed is:

1. A medical device comprising:
   a substrate layer; and
   a surface lubricious layer that is formed on at least a part of a surface of the substrate layer, wherein the surface lubricious layer contains a hydrophilic copolymer comprising:
      structural units derived from a polymerizable monomer (A) having a sulfobetaine structure;

structural units derived from a polymerizable monomer (B) having at least one group selected from the group consisting of a sulfonic acid group (—SO$_3$H), a sulfuric acid group (—OSO$_3$H), a sulfurous acid group (—OSO$_2$H), and groups of salts thereof; and structural units derived from a polymerizable monomer (C) having a photoreactive group, wherein the polymerizable monomer (B) is represented by the following formula (2):

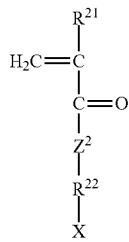

(2)

wherein $R^{21}$ is a hydrogen atom or a methyl group, $Z^2$ is an oxygen atom or —NH—, $R^{22}$ is a straight chain or branched chain alkylene group having 1 to 20 carbon atoms, and X is a group selected from the group consisting of a sulfonic acid group (—SO$_3$H), a sulfuric acid group (—OSO$_3$H), a sulfurous acid group (—OSO$_2$H), and groups of salts thereof.

2. A medical device comprising:

a substrate layer; and a surface lubricious layer that is formed on at least a part of a surface of the substrate layer, wherein the surface lubricious layer contains a hydrophilic copolymer comprising:

structural units derived from a polymerizable monomer (A) having a sulfobetaine structure;

structural units derived from a polymerizable monomer (B) having at least one group selected from the group consisting of a sulfonic acid group (—SO$_3$H), a sulfuric acid group (—OSO$_3$H), a sulfurous acid group (—OSO$_2$H), and groups of salts thereof; and structural units derived from a polymerizable monomer (C) having a photoreactive group, wherein the surface lubricious layer is bound to the substrate layer via the photoreactive group of the hydrophilic copolymer.

3. The medical device according to claim 1, which is a catheter, a stent, or a guide wire.

4. The medical device according to claim 1, wherein the polymerizable monomer (A) is represented by the following formula (1):

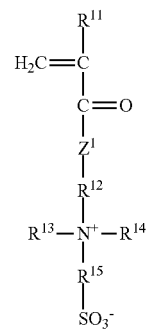

(1)

wherein $R^{11}$ is a hydrogen atom or a methyl group, $Z^1$ is an oxygen atom or —NH—, $R^{12}$ and $R^{15}$ are each independently a straight chain or branched chain alkylene group having 1 to 20 carbon atoms, and $R^{13}$ and $R^{14}$ are each independently a straight chain or branched chain alkyl group having 1 to 20 carbon atoms.

5. The medical device according to claim 1, wherein in formula (1):

$Z^1$ is an oxygen atom, $R^{12}$ and $R^{15}$ are each a straight chain alkylene group having 1 to 3 carbon atoms, and $R^{13}$ and $R^{14}$ are each independently a methyl group.

6. The medical device according to claim 1, wherein the polymerizable monomer (A) includes {2-[(meth)acryloyloxy]ethyl}dimethyl-(3-sulfopropyl)ammonium hydroxide, [3-(methacryloylamino)propyl]dimethyl(3-sulfopropyl)ammonium hydroxide, or a combination thereof.

7. The medical device according to claim 1, wherein in the formula (2):

$Z^2$ is —NH—, $R^{22}$ is a branched chain alkylene group having 3 to 5 carbon atoms, and X is a sulfonic acid group or a group of a salt thereof.

8. The medical device according to claim 1, wherein the photoreactive group is an azide group, a diazo group, a diazirine group, a ketone group, or a quinone group.

9. The medical device according to claim 1, wherein the polymerizable monomer (C) includes, in addition to the photoreactive group, an ethylenically unsaturated group.

10. The medical device according to claim 2, wherein the photoreactive group is an azide group, a diazo group, a diazirine group, a ketone group, or a quinone group.

11. The medical device according to claim 2, wherein the polymerizable monomer (C) includes, in addition to the photoreactive group, an ethylenically unsaturated group.

12. The medical device according to claim 1, wherein the surface lubricious layer is bound to the substrate layer via the photoreactive group of the hydrophilic copolymer.

* * * * *